United States Patent [19]
Hartlaub

[11] 3,951,154
[45] Apr. 20, 1976

[54] LEAD CONNECTOR FOR ELECTRO-MEDICAL DEVICE

[75] Inventor: Jerome T. Hartlaub, New Brighton, Minn.

[73] Assignee: Medtronic, Inc., Minneapolis, Minn.

[22] Filed: Apr. 30, 1974

[21] Appl. No.: 465,526

[52] U.S. Cl. ............................................ 128/419 P
[51] Int. Cl.² .......................................... A61B 1/36
[58] Field of Search .......... 128/2.1 R, 419 P, 421 R, 128/422, 423

[56] References Cited
UNITED STATES PATENTS

| | | | |
|---|---|---|---|
| 3,649,367 | 3/1972 | Purdy | 128/419 P |
| 3,807,411 | 4/1974 | Harris et al. | 128/419 P |
| 3,822,707 | 7/1974 | Adducci et al. | 128/419 P |

FOREIGN PATENTS OR APPLICATIONS 1,379,694  10/1964  France ................... 128/419 PG Primary Examiner—William E. Kamm
Attorney, Agent, or Firm—Walter N. Kirn, Jr.

[57] ABSTRACT

For use with a tissue stimulator device, e.g., a cardiac pacer, a connector element for operatively connecting the generator of the tissue stimulus and the lead which carries the tissue stimulus to the tissue, the connector element having an electrically insulating barrier which results in an open circuit such that current cannot flow through the connector from the power source until the lead is inserted in the connector element thereby by-passing the electrically insulating barrier.

5 Claims, 5 Drawing Figures

LEAD CONNECTOR FOR ELECTRO-MEDICAL DEVICE

This invention relates to electrical tissue stimulating devices and in particular to such a device having an extended useful implantation life.

BACKGROUND OF THE INVENTION

Implantable electrical tissue stimulating devices are well known in the art. For example, one of the better-known tissue stimulators is the cardiac pacer, as shown, for example, in U.S. Pat. No. 3,057,356 to Wilson Greatbatch. These devices, such as the cardiac pacer, generally comprise a pulse generator further comprising a power source (battery) and associated electrical circuitry embedded in, and encapsulated in, or protected by a substance or substances substantially inert to body fluids and tissue. The electrical circuitry of the pulse generator is adapted to be connected by a lead or leads to one or more electrodes which are adapted to be placed adjacent to a remote, desired spot within the human body, such as adjacent to or within myocardial tissue. The cardiac pacer, for example, supplies electrical stimulating pulses to regulate cardiac function in the absence of naturally occurring cardiac pulses.

In implantation of pulse generator and lead, it is common practice for the surgeon to surgically attach or place the electrode distal end of the lead at the desired spot within the human body, that is, in or adjacent to myocardial tissue, and to thereafter connect the lead to a connector assembly associated with the electrical circuitry of the pulse generator in order to commence electrical stimulation of the heart tissue. Prior to making the electrical connection, the surgeon usually measures the electrical stimulation threshold level sufficient to maintain capture of the heart and the sensing threshold level sufficient to trigger the sense amplifier, if any, in the pulse generator circuitry to inhibit the generation of electrical stimulating pulses in the event the heart is functioning normally.

Thereafter, if the threshold levels are adequate, the surgeon usually creates a subcutaneous pocket to receive the encapsulated pulse generator in connective tissue lying just beneath the skin. After the pulse generator is slipped into the pocket, the incision is closed and precautions are taken to avoid build-up of inert body fluids in the pocket and to guard against infections.

At the time of manufacture of the device, the electrical circuitry, including the connector assembly, is connected to the power source. From the time of manufacture of the unit, therefor, current is drawn from the power source through the connector assembly and the unit immediately commences its useful life of from three to five years at the present time. In some instances, the unit may be stored for a period of a year or so before implantation, reducing its implantation life by as much as one-third.

While there are perhaps many approaches which might come to mind to alleviate this shelf degradation problem, it must be kept in mind that any such solution must not entail substantial change in the manner of handling the unit by the surgeon. Surgeons have become accustomed to the rather simple above-described implantation technique and experience has shown them to be resistant to changes in routine for a variety of reasons. Thus, while theoretically possible to provide the units in a dissembled state, e.g., this would require final assembly by the surgeon or others at or near the time of implantation. Thus, assembly would be placed in the hands of those other than the manufacturer's employees who are highly skilled in such procedures. Nor must any solution to the problem entail a nonconventional manipulative procedure foreign to the surgeons past modus operandi lest the procedure be mishandled or perhaps forgotten. It is to be appreciated, of course, that in any surgical procedure additional demands placed on the surgeon or his team are to be avoided if at all possible.

In this context, it is an object of the present invention to provide a tissue stimulating device having an extended useful implantation life.

A further object is to provide a tissue stimulating device wherein power is not dissipated from the power source until the time of implantation.

Another object is a device of the foregoing type which does not entail any change in handling procedures by the operating team.

SUMMARY OF THE INVENTION

These and other objects are accomplished in the present invention wherein, in combination with a tissue stimulator having generating means for producing tissue stimulation energy, lead connector means electrically associated with the generator means, and lead means attachable to the lead connector means for conducting the stimulation energy to remote body tissues, there is provided an improvement in lead connector means which comprises electrical insulating means interposed between portions of said lead connector means whereby said electrical continuity through said connector means is interrupted when said lead means is absent.

As an example, by means of the electrical insulating means the battery or power source of the generator is in effect isolated and not connected to the electrical circuitry. Only when the lead means is connected to the connector means is the battery connected, directly or indirectly, to the connector thereby activating the unit to provide the tissue stimulating energy.

In a preferred embodiment of the invention, the connector means is a bifurcated structure divided into two electrically conductive sections or portions by an electrically insulating layer which may also bond the two portions together. A receptacle is provided for insertion therein of a conventional lead pin, the lead pin being in simultaneous electrical contact with the two electrically conductive portions of the connector means and thereby providing an electrically conductive bridge from one portion to the other. The electrical insulating layer is thus bypassed, and the battery thereby connected to the connector means to provide generation of the tissue stimulating energy.

From a structural standpoint, the principal variation in structure involves the presence of the electrically insulating barrier which in an electrical sense provides a circuit interrupter across the connector means. Conventional connector means are of a unitary construction and contain, in addition to the receptacle for the lead means, a threaded bore which communicates with the receptacle. This threaded bore threadably engages a set screw which, after insertion of the lead pin in the receptacle, is screwed down onto the lead pin to hold the same in place. In the preferred embodiment of the present invention, the set screw or its equivalent is retained for its former purpose and is operated in precisely the same manner as before. However, in addition to providing a lead retaining function, the set screw also ensures good electrical contact between the lead pin and the two portions of the lead connector. In fact, the set screw now becomes a part of the electric circuitry.

DESCRIPTION OF THE PREFERRED EMBODIMENT

Figure 1:
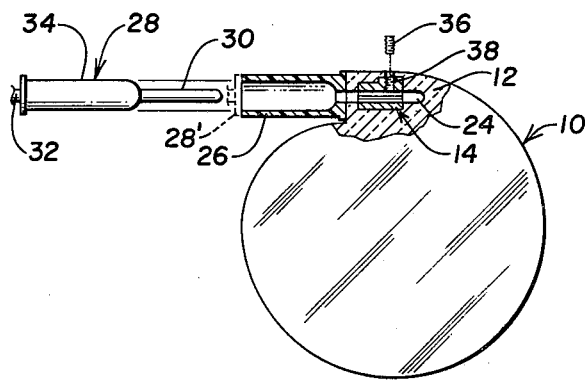
FIG. 1 is a cutaway view of a terminal portion of a conventional generator housing the present invention.

FIG. 1 shows generator device 10 which, except for the connector means of this invention, is conventional in shape and construction. The generator 10 may comprise a battery-power source and a miniaturized electrical circuit (neither shown) for sensing the spontaneous myocardial voltage and for delivering electrical stimulating impulses at a preset pacing rate. The electrical components of the generator 10 are encapsulated in a transparent epoxy resin encapsulant 12 that is compatible with and substantially inert to body fluids and tissue. A connector 14 is embedded in encapsulant 12. Connector 14 is divided into two portions 16 and 18 by electrical insulating layer 20. Portions 16 and 18 are made of electrically conductive material, preferably an inert, body compatible, machinable metal such as titanium. A preferred electrical insulating layer is an epoxy resin which may be of the same composition as encapsulant 12. Other suitable materials include various resins such as phenolics and polyesters. The thickness of insulating layer 20 may vary widely depending upon the electrical characteristics of the material itself. A thickness of about 3-7 mm. may be suitable. Connector 14 has a longitudinally extending central shaft 22 which communicates at the rear end with chamber 24 and at the forward end with lead collar 26 made of silicone rubber. A conventional lead 28 is shown in position for insertion into collar 26 and the same lead (designated 28') is shown in place in connector 14. Lead 28 includes an electrically conductive terminal pin 30 which, when in position, is located in shaft 22 and protrudes into chamber 24. Lead 28 also includes a centrally located braided electrical conductor 32 ensheathed in an electrically insulating covering 34 which is composed of a material such as silicone rubber which is compatible with and inert to body fluids and tissue.

Terminal pin 30 is held in place in shaft 22 by means of an electrically conductive set screw 36 threadably engaging threaded bore 38.

Figure 2:
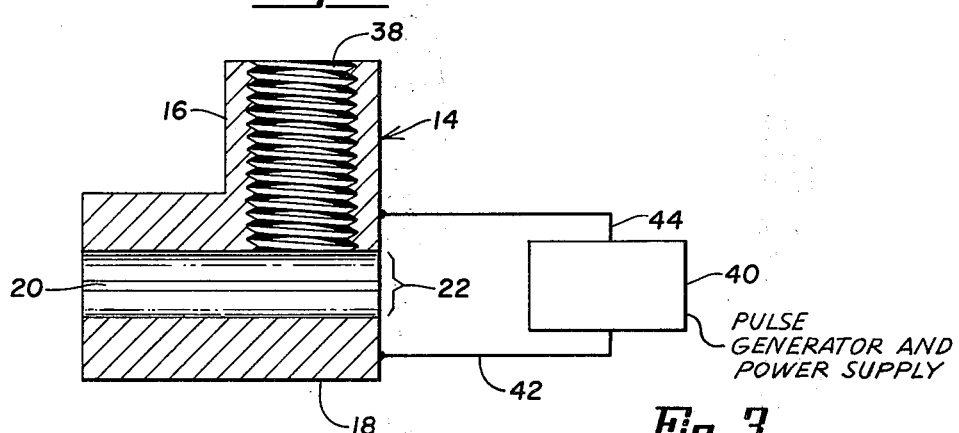
FIG. 2 is a cross-sectional view of a preferred embodiment of the present invention.

FIG. 2 is an enlarged view of connector 14. Box 40, denoting the conventional circuitry and power source of a pulse generator 10, is connected to connector 14 by leads 42 and 44. Lead 42 is electrically connected to portion 18 of connector 14 whereas lead 44 is electrically connected to portion 16. Due to the presence of the electrical insulating gap between portions 16 and 18 (provided by the combination of insulating layer 20 and the air occupying shaft 22) there is no electrically continuous path between leads 42 and 44 in the situation depicted in FIG. 2.

Figure 4:
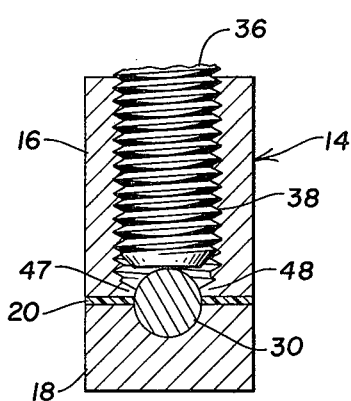
FIG. 4 is a sectional view taken along line 4—4 of FIG. 3.
Figure 3:
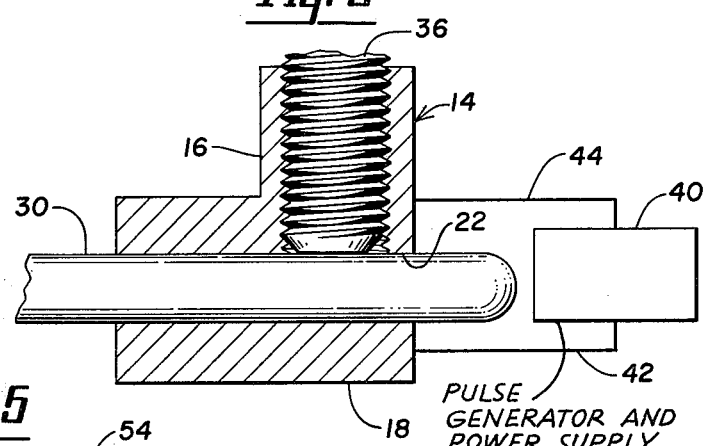
FIG. 3 is a cross-sectional view of the embodiment of FIG. 2 with the lead pin and set screw in operative position.

In FIGS. 3 and 4, however, electrically conductive terminal pin 30 occupies shaft 22 thereby providing an electrically continuous path between portions 16 and 18 and thus an electronic circuit is connected to the power source and circuitry of box 40 and the connector 14 and pin 30. Note that in FIG. 4, the portion 16 forming the terminal portion of threaded bore 38 has inward and downward depending shoulders 46 and 48 which are contacted by terminal pin. Set screw 36, which has a notched head (not shown) engageable by a tool for advancing and retracting screw 36 in bore 38, engages pin 30 to provide not only a retaining hold on pin 30 but also electrical contact with portion 16 of connector 14. The working end of screw 36 has a sharp ridge which actually penetrates pin 30 to provide a cold weld thereby ensuring retention of pin 30 in place during use. It is preferred for ease of insertion of lead 28 into connector 14 that shaft 22 be slightly larger in cross-section than the cross-section of pin 30 and thus set screw 36 or some other retaining means is preferred to ensure both physical retention and electrical continuity.

The method of attaching the lead to the generator is the same for the device of this invention as for pulse generators previously extensively used by surgeons. The method of attachment for bipolar devices (two leads) comprises the following enumerated steps.

1. After the lead is brought out of the body at the position where the pulse generator is to be implanted, the surgeon cleans the lead connector ends and coats the terminal pins and lead collars with a silicone oil lubricant to facilitate entry into the silicone rubber boots of the pulse generator terminal assembly;

2. After checking the proper polarity of the lead connector end with respect to the positive and negative connector terminals of the pulse generator, the surgeon pushes the correct polarity lead connector ends into the respective silicone rubber boots until each lead collar snaps into place in the silicone rubber boots and both terminal pins are visible through the set screw holes;

3. After placing a socket set screw on a hex wrench (both items provided with the pulse generator by the manufacture), the surgeon inserts and tightens the respective set screw against the terminal pins with the hex wrench while making certain that the terminal pins do not retract as the set screw is tightened;

4. After the two set screws are tightened down, the surgeon then selects a nylon filler screw and rubber O-ring and tightens the filler screw into the seat and the threaded bore of the connector block with a second tool which comprises an ordinary screwdriver (all items provided with the pulse generator by the manufacturer); and 5. Thereafter, the surgeon tightens each silicone rubber boot with respect to the lead by means of nonabsorbable sutures placed in the grooves encircling the silicone rubber boots.

The above-described method applies to implantable tissue stimulators such as cardiac pacers manufactured by many different organizations. Some manufacturers, however, alter step 4 by eliminating the nylon filler screw 48 and instead recommending that the physician seal the holes to the set screws with a medical adhesive.

Figure 5:
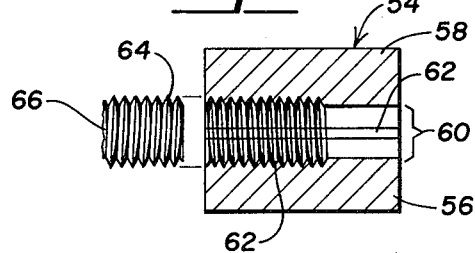
FIG. 5 is a cross-sectional view of another embodiment of the present invention.

FIG. 5 illustrates another embodiment of the invention. Connector 54 includes electrically conductive portions 56 and 58 separated by shaft 60 and insulating barrier layer 62. Shaft 60, which extends the length of connector 54, has thread means 62 which are adapted to engage the matching threads 64 of electrically conductive lead pin 66. Upon screwing threaded lead pin 66 into shaft 60, the insulating barrier layer 62 is bypassed, thereby providing an electrically continuous path between both sections of connector 54. In this embodiment the threaded engagement between the lead pin 66 and shaft 60 eliminates the need for the bore and set screw of the embodiment of FIGS. 1–4.

Depending upon the circuitry between the power source and the connector of this invention, the latter can influence the current drain from the power source by reducing the current drain to zero or some fraction of the current drain which occurs during operation of the device. In the case of a direct, uninterrupted connection from the power source to the connector means, the connector means of this invention serves as an on-off switch, with substantially no current being drawn from the power source prior to insertion of the lead pin. In the case of an indirect connection from the power source to the connector means, where the power source is also part of a circuit not including the connector means, some current is being drawn from the power source. Insertion of the lead pin into the connector means introduces the connector means into the circuitry. In a generic sense, this connector means is thus seen to function as a circuit modifier. One advantage to the latter type of device is that where a small but detectable current drain is occurring at all times such current drain can provide a quality control signal for checking whether the unit is functioning properly prior to use.

Manufacture of the connector means of this invention can be accomplished by well-known processing techniques such as milling, tapping, drilling and machining. The connector block may be initially formed into a single block, then divided into two portions of the shapes herein illustrated, the receptacle and bore holes made, the insulating layer applied, and the two portions rejoined. The insulating layer may perform as an adhesive or the function of holding the two portions of the connector means may be performed by other external means such as the epoxy encapsulant which encases the entire connector means in the housing of the tissue stimulator device.

The connector means may be employed singly in the case of unipolar units or doubly in the case of bipolar units. In either case, appropriate circuitry connecting the connector means to the power source is provided for the task to be performed by the connector means. In the preferred embodiment illustrated in FIGS. 1–4, no additional parts are required nor are any additional or different manipulative steps required by the operating team. In the embodiment of FIG. 5, while additional steps are not required, the lead pin is twisted or screwed into position in the connector means rather than merely pushed. On the other hand, in this embodiment, the step of tightening the set screw is eliminated.

What is claimed is:

1. In combination with a tissue stimulator having pulse generator means electrically interconnected with a source of electrical energy for producing electrical tissue stimulation impulses, lead connector means electrically interconnected with said generator means, and electrically conductive lead means attachable to said lead connector means for conducting the stimulation impulses to remote body tissue, the improvement in lead connector means for inhibiting the production of the stimulation impulses which comprises electrical insulating means providing an insulating barrier between first and second electrically conductive portions of said lead connector means, said first and second portions and said insulating means defining a receptacle providing a cavity for insertion therein of said lead means, said first and second portions extending partially around the circumference of said cavity and said insulating means being circumferentially interposed between said first and second portions, and circuit means for electrically interconnecting said source of electrical energy with said first and second portions of said lead connector means and said generator means, whereby said electrical interconnection between said generator means and said source of electrical potential is only effective when said electrically conductive lead means is attached to said first and second portions of said lead connector means.

2. A tissue stimulator device comprising pulse generator means for producing electrical tissue stimulation impulses, electrically conductive lead means for conducting the stimulation impulses to remote body tissue, said lead means having an electrically conductive terminal, and at least one lead connector means electrically connected to said generator means for attachably receiving said terminal of said lead means, said lead connector means comprising electrically conductive first and second portions each connected to said generator means and an electrically nonconductive third portion, said first, second, and third portions defining a receptacle providing a cavity for insertion therein of said lead means, said first and second portions extending partially around the circumference of said cavity and said third portion being circumferentially interposed between said first and second portions to provide an electrically nonconductive barrier between said first and second portions, said barrier being electrically bridged by said terminal when attached to said connector means whereby said first and second portions are electrically connected to one another.

3. The tissue stimulator device of claim 2 wherein said connector means further comprises bore means communicating with said receptacle, and electrically conductive retaining means located in said bore means for retaining said lead terminal in said receptacle.

4. The tissue stimulator device of claim 3 wherein said bore means is threaded to receive said retaining means.

5. The device of claim 2 wherein said receptacle and said lead terminal are compatibly threaded.

* * * * *